(12) United States Patent
Eda (10) Patent No.: US 12,394,579 B2
(45) Date of Patent: Aug. 19, 2025

(54) PRESS BUTTON STRUCTURE OF ULTRASONIC DIAGNOSTIC APPARATUS

(71) Applicant: FUJIFILM Healthcare Corporation, Kashiwa (JP)

(72) Inventor: Masato Eda, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 108 days.

(21) Appl. No.: 18/200,077

(22) Filed: May 22, 2023

(65) Prior Publication Data
US 2023/0402238 A1 Dec. 14, 2023

(30) Foreign Application Priority Data
Jun. 8, 2022 (JP) .................................. 2022-093049

(51) Int. Cl.
*H01H 13/14* (2006.01)
*A61B 8/00* (2006.01)
*H01H 13/10* (2006.01)

(52) U.S. Cl.
CPC ............. *H01H 13/14* (2013.01); *A61B 8/467* (2013.01); *H01H 13/10* (2013.01)

(58) Field of Classification Search
CPC ........ H01H 13/14; H01H 13/10; H01H 13/06; H01H 3/12; H01H 13/84; H01H 13/85; A61B 8/467; A61B 8/4444; A61B 8/4455; A61B 8/44; A61B 8/00
See application file for complete search history.

(56) References Cited

U.S. PATENT DOCUMENTS

| 7,705,258 B2 * | 4/2010 | Geldmacher ...... G07C 9/00944 200/341 |
| 7,740,166 B2 * | 6/2010 | Takeuchi ............... H01H 13/48 200/406 |
| 2009/0301852 A1 * | 12/2009 | Keist ...................... B60K 35/10 200/341 |

FOREIGN PATENT DOCUMENTS

| JP | 2005-296487 A | 10/2005 |
| JP | 2006-020755 A | 1/2006 |

* cited by examiner

*Primary Examiner* — Lheiren Mae A Caroc
(74) *Attorney, Agent, or Firm* — Paul Teng (57) ABSTRACT

A press button structure includes a substrate, a movable contact member, a guide member, and a cap member composed of an upper cap member and a lower cap member. The movable contact member includes a base, a protrusion having a lower face including a movable contact, and an elastic member connecting the base and the protrusion. The guide member is cylindrical and is disposed to surround a side of the protrusion. The lower cap member covers the side face of the protrusion and is located between the side wall of the protrusion and the guide member. More specifically, the lower cap member is disposed adjacent and opposite an inner side face of the guide member in a manner that the lower cap member is slidable upward and downward along the inner side face of the guide member.

4 Claims, 8 Drawing Sheets

PRESS BUTTON STRUCTURE OF ULTRASONIC DIAGNOSTIC APPARATUS

CROSS REFERENCE TO RELATED APPLICATION

This application claims priority to Japanese Patent Application No. 2022-093049 filed on Jun. 8, 2022, which is incorporated herein by reference in its entirety including the specification, claims, drawings, and abstract.

TECHNICAL FIELD

The present specification discloses a press button structure of an ultrasonic diagnostic apparatus.

BACKGROUND

Ultrasonic diagnostic apparatuses that perform ultrasonic diagnosis while transmitting and receiving ultrasonic waves to and from a subject have been known. As described in JP 2005-296487 A, for example, an ultrasonic diagnostic apparatus includes an operation panel that is operated by a user such as a doctor to input instructions in the ultrasonic diagnostic apparatus. The operation panel of the ultrasonic diagnostic apparatus includes a plurality of operation elements including a press button.

There has been a disadvantage of a press button of an ultrasonic diagnostic apparatus in that pressing different locations on a surface of the press button results in different senses of pressing or feeling of pressing. Referring to FIGS. 5 to 9, this disadvantage will be described in relation to a conventional press button structure.

Figure 5:
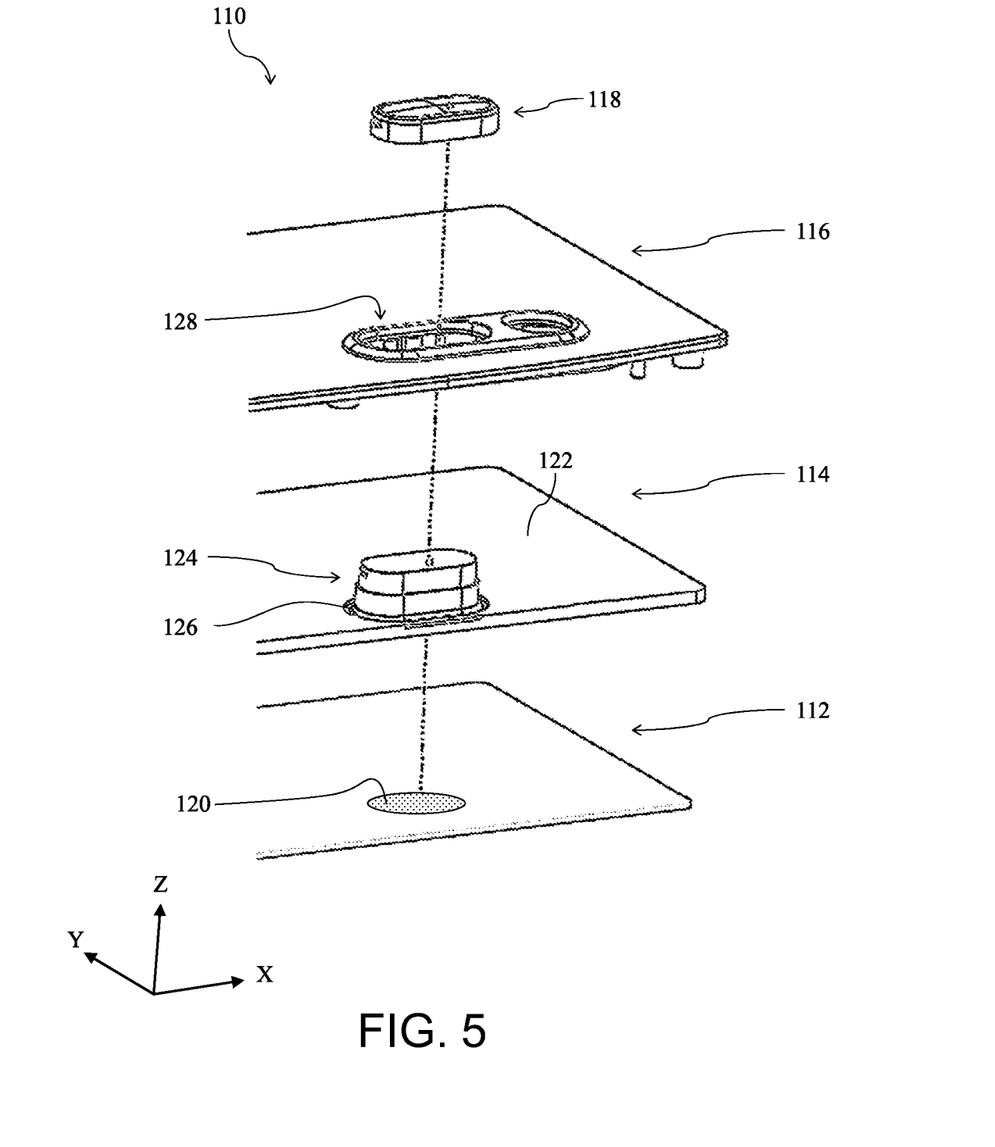
FIG. 5 is an exploded view of a press button structure according to a prior art example.
Figure 6:
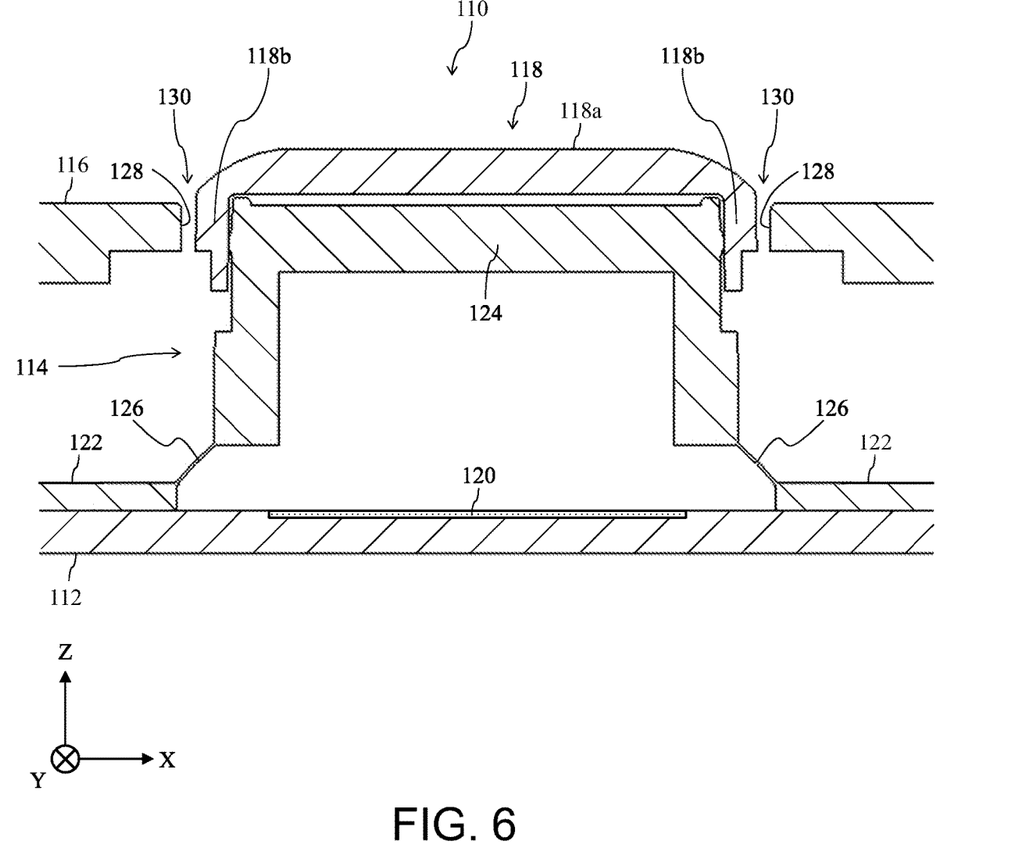
FIG. 6 is a vertical cross sectional view of the press button structure according to the prior art example.

FIG. 5 is an exploded view of a press button structure 110 of an ultrasonic diagnostic apparatus according to a prior art example, and FIG. 6 is a vertical cross sectional view of the press button structure 110. In FIG. 5 and FIG. 6, an X-axis denotes a horizontal direction along a width of the ultrasonic diagnostic apparatus, a Y-axis denotes a horizontal direction along a depth of the ultrasonic diagnostic apparatus that is normal to the X-axis, and a Z-axis denotes a direction along a height of the ultrasonic diagnostic apparatus (the forward direction of the Z-axis being upward).

The press button structure 110 includes a substrate 112, a movable contact member 114 disposed over (outside) the substrate 112, a casing 116 disposed further above the movable contact member 114, and a cap member 118.

The substrate 112 is an electronic substrate including a conductor pattern, and a fixed contact 120 is disposed on an upper surface of the substrate 112.

The movable contact member 114 includes a base 122, a protrusion 124 having a convex shape protruding upward, and an elastic member 126 connecting the base 122 and the protrusion 124. A movable contact (not shown) is disposed on a lower face of the protrusion 124. The elastic member 126 urges the protrusion 124 upward, and, in a natural state, holds the protrusion 124 to keep the movable contact of the protrusion 124 and the fixed contact 120 of the substrate 112 apart from each other. In the illustrated example of the press button structure 110, the elastic member 126 has a circular shape, and, in the natural state illustrated in FIG. 6, assumes a skirt shape sloped outwardly downward. An inner edge of the circular elastic member 126, or an upper edge in its natural state, is connected to a side wall of the protrusion 124, or a lower edge of the side wall in the example of the press button structure 110, and an outer edge of the elastic member 126, or a lower edge in its natural state, is connected to the base 122.

The casing 116 forms an outer surface of the ultrasonic diagnostic apparatus, and more specifically, of the operation panel. The casing 116 includes a button hole 128 to allow the cap member 118 to pass through.

The cap member 118 includes a top plate 118a extending horizontally and side walls 118b protruding downward from an edge of the top plate 118a. The cap member 118 is mounted on the protrusion 124 to cover a top face and part of a side face of the protrusion 124.

In response to the user depressing of the top plate 118a of the cap member 118, the elastic member 126 elastically deforms to push the protrusion 124 downward. This brings the movable contact disposed on the lower face of the protrusion 124 into contact with the fixed contact 120, and operation of the press button is detected.

Figure 7:
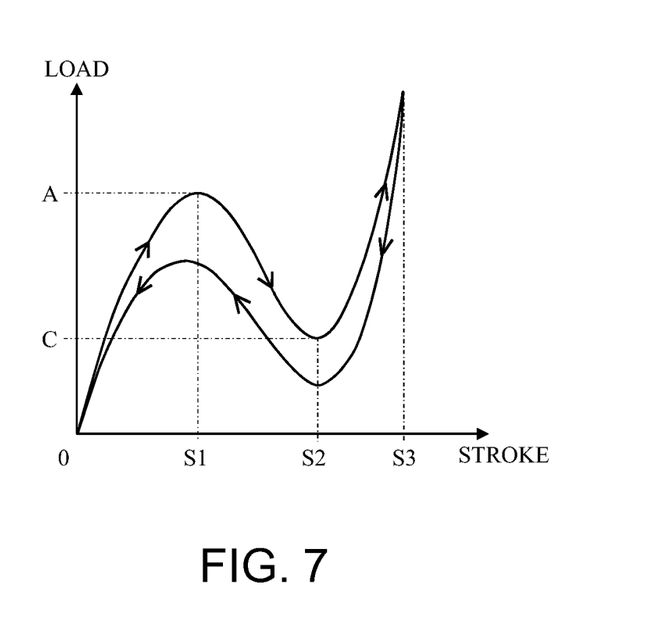
FIG. 7 illustrates a feeling curve.

The sense of pressing or feeling of pressing of the press button will be described. FIG. 7 shows a feeling curve. In the graph shown in FIG. 7, the horizontal axis indicates a stroke of the protrusion 124 (the vertical position of the protrusion 124) and the vertical axis indicates a load on the protrusion 124, which can be regarded as a magnitude of a reaction force of the elastic member 126 against the pressing force applied to the protrusion 124. A graph indicating the relationship between the stroke of the press button and the load is referred to as a feeling curve.

In the natural state, the elastic member 126 has a skirt shape described above; therefore, between stroke 0 and stroke S1, the load increases with the pressing amount of the protrusion 124. At stroke S1, the elastic member 126 having a skirt shape extends horizontally into a horizontally parallel circular shape. Thereafter, the reaction force of the elastic member 126 is lowered, and between stroke S1 and stroke S2, the load decreases with the pressing amount of the protrusion 124. At stroke S2, the movable contact comes into contact with the fixed contact 120. Then, between stroke S2 and stroke S3, the protrusion 124 moves with elastic deformation of the elastic member 126 to cause an increase in the load. Upon stop of pressing of the protrusion 124 by the user, the upward urging force of the elastic member 126 returns the stroke of the protrusion 124 to 0.

Assuming that the load at stroke S1, or a maximum load required until the press button is switched on, is load A, and the load at stroke S2, or a load after the press button is switched on, is load C, an index called click rate is conventionally calculated according to the following formula:

$$\{(A-C)/A\}\times 100[\%]$$

Figure 8:
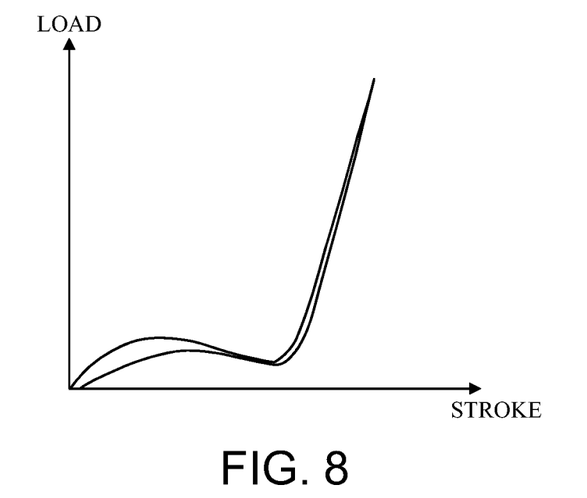
FIG. 8 illustrates a feeling curve obtained by a user pressing a center of a top plate of a cap member in a plan view, in the press button structure according to the prior art example.
Figure 9:
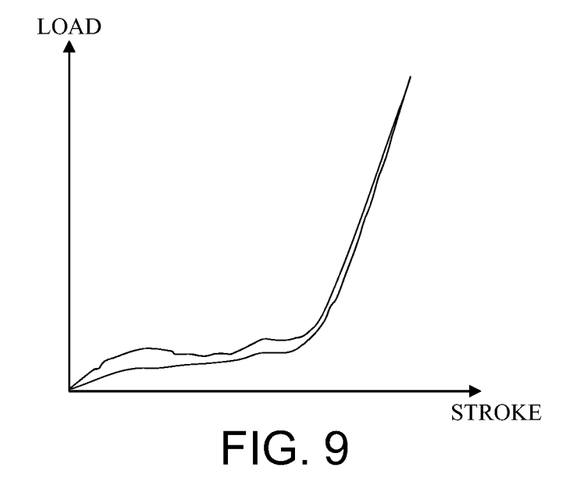
FIG. 9 illustrates a feeling curve obtained by a user pressing an edge of a top plate of a cap member in a plan view, in the press button structure according to the prior art.

The click rate is an index that represents the user's sense of pressing of the press button. Various click rates or click feeling obtained by pressing the surface of the press button at different locations indicate various senses of pressing obtained by pressing the surface of the press button at different locations. FIG. 8 shows a feeling curve obtained by the user's pressing the center of the top plate 118a of the cap member 118 in a plan view, and FIG. 9 shows a feeling curve obtained by the user's pressing an edge of the top plate 118a in a plan view. The feeling curve shown in FIG. 8 represents a proper sense of pressing that is intended by a designer of the press button, whereas the feeling curve shown in FIG. 9 does not represent the proper sense of pressing. The click rates or click feelings obtained from these feeling curves are obviously different from each other, in which case, the user feels different senses of pressing of the press button.

One of the factors that cause the feeling curve shown in FIG. 9 lies in the movable portion of the press button, which is the protrusion 124 in the press button structure 110, being unable to move straight up and down. In the example illustrated in FIG. 6, for example, in response to user's pressing the right side of the top plate 118a, the elastic member 126 deforms only on the right side to cause the protrusion 124 to be inclined downward to the right. Thereafter, further depression of the protrusion 124 by the user causes delayed deformation of the elastic member 126 on the left side after the deformation of the elastic member 126 on the right side to further change the position (inclination) of the protrusion 124. Such an inclination of the protrusion 124 can cause the distorted feeling curve as illustrated in FIG. 9.

Here, a gap 130 between the side wall 118b of the cap member 118 and the inner wall of the button hole 128 permits the inclination of the protrusion 124. While narrowing the gap 130 may inhibit the inclination of the protrusion 124, it is not easy to narrow the gap 130, for the following reason. Specifically, an ultrasonic diagnostic apparatus may suffer from a problem in that foreign matter such as dust and echo jelly enter and fix to the gap 130 to thereby prevent the upward and downward movement of the cap member 118 or the protrusion 124. To prevent this problem, it is necessary to keep the gap 130 at a predetermined width or greater, and this prevents narrowing of the gap 130.

Also, the user of the ultrasonic diagnostic apparatus may hold an ultrasonic probe with one hand and operate the press button with the other hand while viewing an ultrasound image displayed on the display. In this case, the user cannot properly press the center of the press button, making the above-described problem apparent particularly in ultrasonic diagnostic apparatuses.

In addition, the protrusion 124 having an elongated shape extending in one direction in a plan view as illustrated in FIGS. 5 and 6 is particularly likely to cause variations in the sense of pressing corresponding to different pressing locations.

A press button structure of an ultrasonic diagnostic apparatus disclosed in the present specification is therefore aimed toward reducing variations in the sense of pressing obtained by pressing different locations on a surface of the press button disposed in an ultrasonic diagnostic apparatus.

SUMMARY

A press button structure of an ultrasonic diagnostic apparatus disposed in the present specification includes a substrate including a fixed contact, a movable contact member disposed over the substrate, a cylindrical guide member, and a cap member. The movable contact member includes a base, a protrusion, and an elastic member. The protrusion has a convex shape protruding upward and has a movable contact on a lower face of the protrusion, and the movable contact is to be in contact with the fixed contact. The elastic member connects the base and the protrusion, and, in a natural state, urges the protrusion upward to hold the protrusion in a manner that the movable contact and the fixed contact are separated. The elastic member has an upward reaction force that changes in accordance with a pressing amount of the protrusion that is pressed downward. The cylindrical guide member is disposed to surround a side of the protrusion. The cap member is mounted on the protrusion and includes a top plate covering a top face of the protrusion and a side wall covering a side face of the protrusion. The side wall of the cap member is disposed adjacent and opposite an inner side face of the guide member in a manner that the side wall is slidable upward and downward along the inner side face.

This configuration allows the side wall of the cap member to come into contact with the guide member to thereby inhibit inclination of the protrusion. Specifically, the configuration enables the protrusion to move upward and downward with the inclination of the protrusion being inhibited. This provides a substantially proper feeling curve regardless of the location on the top plate of the cap member to be pressed by the user, and thus reduces variations in the sense of pressing obtained by pressing different locations on the surface of the press button.

The side wall of the cap member may include a flange that protrudes outward in a region above an upper edge of the guide member and covers an upper part of a gap between the side wall of the cap member and the inner side face of the guide member.

This configuration inhibits entry of foreign matter such as dust and echo jelly into the gap between the side wall of the cap member and the inner side face of the guide member.

The flange may extend to a point above an outer edge of the guide member.

This configuration further inhibits entry of foreign matter into the gap between the side wall of the cap member and the inner side face of the guide member.

The press button structure may further include a casing disposed over the movable contact member and having a button hole to allow the cap member to pass through. The cap member may include an upper cap member including the top plate and being inserted through the button hole, and a lower cap member disposed below the casing and including the flange. The upper cap member and the lower cap member are detachable.

This configuration facilitates change of a sheet including printed letters that is inserted between the top plate of the cap member and the protrusion.

The protrusion may have an elongated shape extending along one direction in a plan view.

This configuration reduces variations in the sense of pressing obtained by pressing different locations on a press button surface in a protrusion having an elongated shape which is likely to cause variations in the sense of pressing in accordance with the pressing location.

The press button structure of an ultrasonic diagnostic apparatus disclosed in the specification enables reduction in variations of the sense of pressing obtained by pressing different locations on a surface of a press button disposed in an ultrasonic diagnostic apparatus.

BRIEF DESCRIPTION OF DRAWINGS

An embodiment of the present disclosure will be described based on the following figures, wherein.

DESCRIPTION OF EMBODIMENTS

Figure 1:
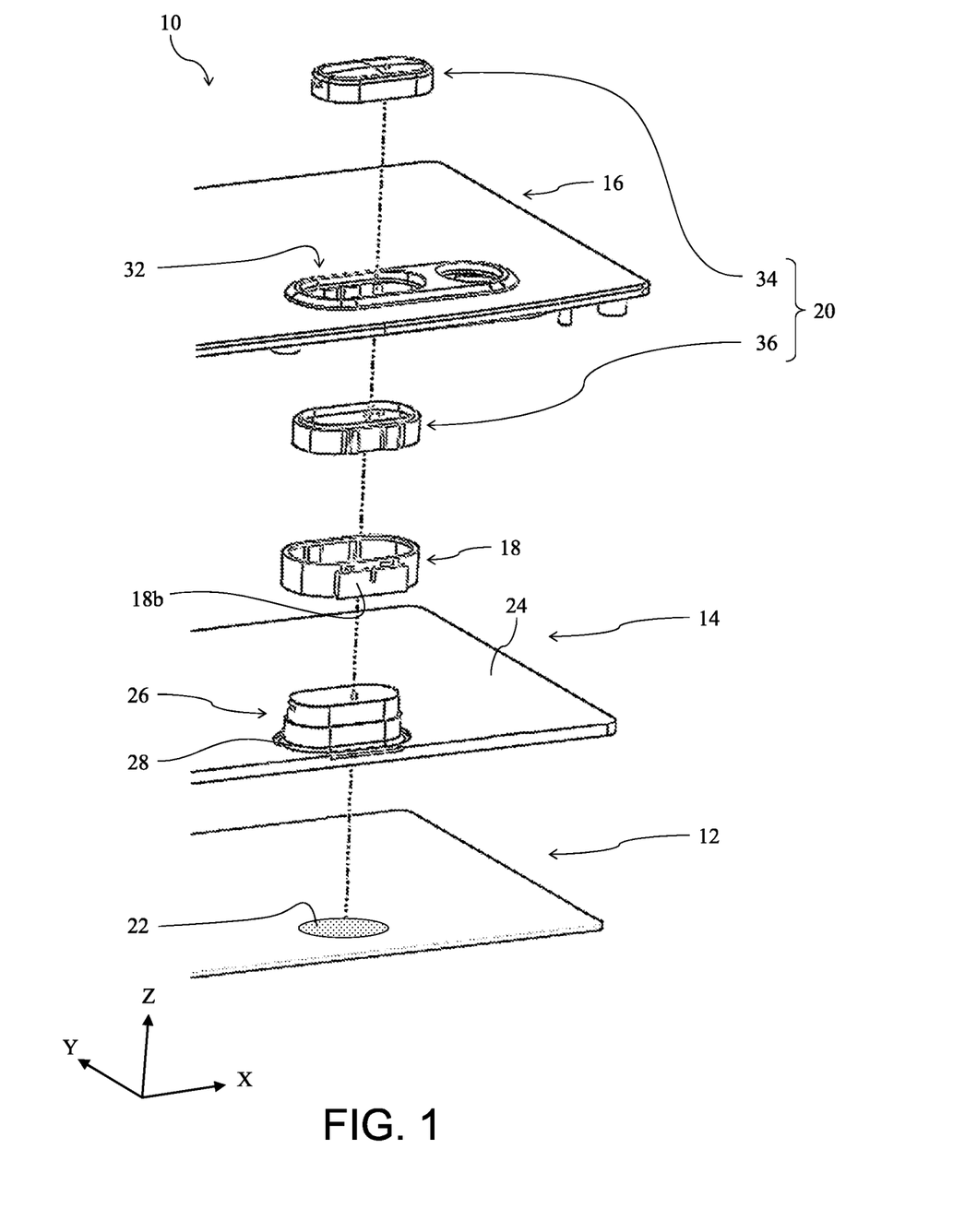
FIG. 1 is an exploded view of a press button structure according to an embodiment.
Figure 2:
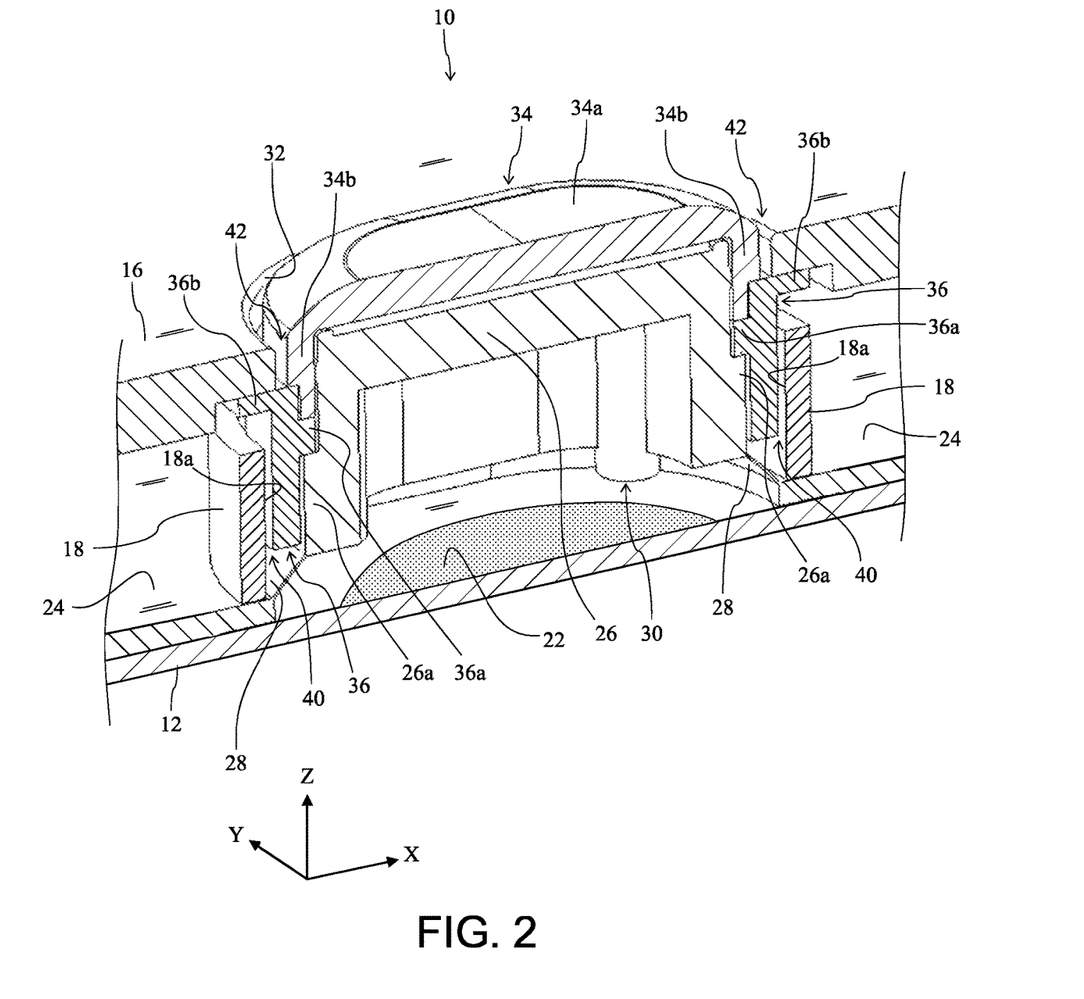
FIG. 2 is a perspective cross sectional view of the button structure according to the embodiment.
Figure 3:
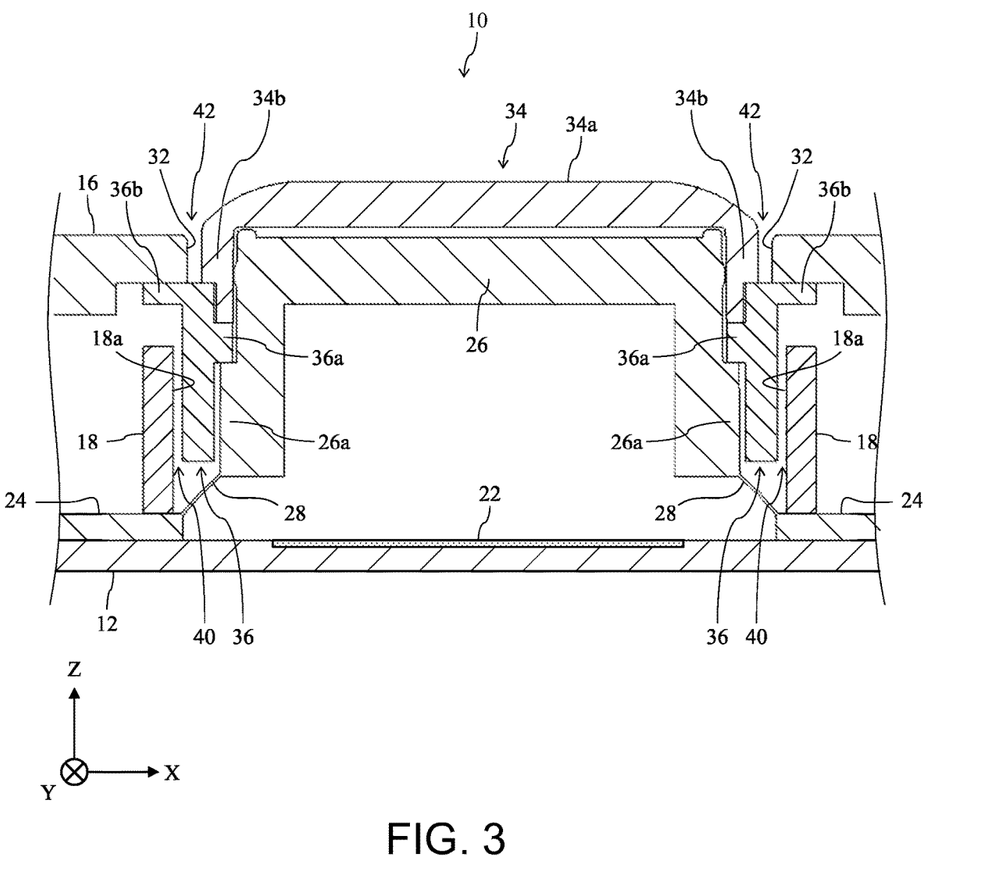
FIG. 3 is a vertical cross sectional view of the button structure according to the embodiment.
Figure 4:
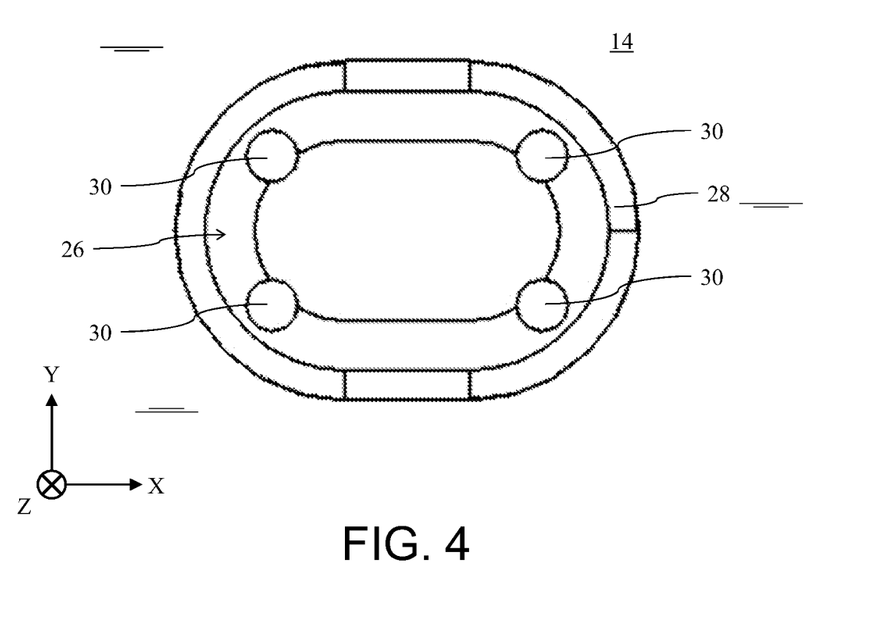
FIG. 4 is a bottom view of a movable contact member.

FIG. 1 is an exploded view of a press button structure 10 according to the present embodiment; FIG. 2 is a perspective cross sectional view of the press button structure 10; FIG. 3 is a vertical cross sectional view of the press button structure 10; and FIG. 4 is a bottom view of a movable contact member 14. In FIG. 1 to FIG. 4, an X-axis indicates a horizontal direction along the width of an ultrasonic diagnostic apparatus, a Y-axis indicates a horizontal direction vertical to the X-axis, which extends along the depth of the ultrasonic diagnostic apparatus, and a Z-axis indicates a direction along the height, with the forward direction along the Z-axis indicating upward.

The press button structure 10 includes a substrate 12, a movable contact member 14, a casing 16, a guide member 18, and a cap member 20.

The substrate 12 is an electronic substrate including a conductor pattern, and includes a fixed contact 22 on a top surface.

The movable contact member 14 is disposed over (outside) the substrate 12, and includes a base 24, a protrusion 26 having a convex shape protruding upward, and an elastic member 28 connecting the base 24 and the protrusion 26.

While in the present embodiment the base 24 has a sheet-like shape extending in parallel to the substrate 12, the shape of the base 24 is not limited to this example.

The protrusion 26 has a convex shape protruding upward. In the present embodiment, the protrusion 26 protrudes upward from the sheet-like base 24. Further, in the present embodiment, the protrusion 26 has an elongated shape extending along the X-axis in a plan view. Specifically, the protrusion 26 has an elliptical shape extending along the X-axis in a plan view. As illustrated in FIG. 2 and FIG. 3, the protrusion 26 is hollow and is opened downward. The protrusion 26 includes a swelling portion 26a protruding sideward in a lower half portion of its side wall. Further, as illustrated in FIG. 4, the protrusion 26 includes movable contacts 30 on its lower face. In this embodiment, the protrusion 26 includes a plurality of (four) movable contacts 30.

The elastic member 28 has elasticity and urges the protrusion 26 upward with an elastic force. The elastic member 28, in its natural state, holds the protrusion 26 to keep the movable contact 30 of the protrusion 26 and the fixed contact 22 of the substrate 12 apart from each other. While in the present embodiment the movable contact member 14 is entirely made of a resin such as rubber and is entirely elastic, at least the elastic member 28 may be elastic. In the present embodiment, the elastic member 28 has a circular shape, and assumes a skirt shape sloped outward and downward in the natural state illustrated in FIG. 2 and FIG. 3. The inner end of the circular elastic member 28 (the upper end in the natural state) is connected with the side wall of the protrusion 26 (the lower end of the swelling portion 26a in the present embodiment), and the outer end of the elastic member 28 (the lower end in the natural state) is connected with the base 24.

The casing 16 is disposed on top of the movable contact member 14 to form an outer surface of the ultrasonic diagnostic apparatus (more specifically, of the operation panel). The casing 16 is made of resin and includes a button hole 32 to allow the protrusion 26 and the cap member 20 (particularly, an upper cap member 34) to pass through.

The guide member 18 has a cylindrical shape and is disposed to surround the side wall of the protrusion 26. The guide member 18 is made of resin. In the present embodiment, the guide member 18 is made of polyoxymeethylene (POM) resin. POM has a low coefficient of friction (easy to slip), a high abrasion resistance, and a high fatigue resistance. In the present embodiment, the protrusion 26 has an elliptical shape extending along the X-axis in a plan view, as described above, and therefore the guide member 18 also has an outer shape and inner hole having a corresponding elliptical shape in a plan view.

The guide member 18 is placed from above to surround the protrusion 26 with the casing 16 being removed. Mounting the casing 16 in this state causes the guide member 18 to be sandwiched and held between the base 24 of the movable contact member 14 and the casing 16. Specifically, the guide member 18 is held with a hook receiver 18b (see FIG. 1) disposed on the guide member 18 coming into engagement with a hook (not shown) disposed on the bottom of the casing 16. The guide member 18 is thus detachable with respect to the protrusion 26.

The cap member 20 is attached to the protrusion 26 to cover the top face and at least part of the side face of the protrusion 26. The cap member 20 is made of resin such as polycarbonate. In the present embodiment, the cap member 20 includes an upper cap member 34 and a lower cap member 36 which are detachably connected with each other. However, the cap member 20 need not be separated into the upper cap member 34 and the lower cap member 36.

The upper cap member 34 includes a top plate 34a extending horizontally to cover the top face of the protrusion 26 and a side wall 34b protruding from an edge of the top plate 34a. The upper face of the top plate 34a serves as a pressing face that is to be pressed by the user. The upper cap member 34 is inserted into the button hole 32 along with the protrusion 26.

The lower cap member 36 has a substantially cylindrical shape which corresponds to the shape of the inner hole of the guide member 18 in a plan view. As, in the present embodiment, the inner hole of the guide member 18 has an elliptical shape in a plan view as described above, the lower cap member 36 has a corresponding outer shape that is an elliptical shape in a plan view.

The lower cap member 36 is detachably connected to a lower edge of the side wall 34b of the upper cap member 34. In the present embodiment, the lower cap member 36 is disposed below the (lower edge of) the casing 16. In other words, the lower cap member 36 is not inserted through the button hole 32.

The lower cap member 36 includes, in an upper portion of its inner side face, an inward protrusion 36a protruding inward. The inward protrusion 36a is disposed along the entirety or part of the circumferential direction. The inward protrusion 36a has a lower face that is in contact with the upper face of the swelling portion 26a of the protrusion 26. Thus, the lower cap member 36 is disposed in contact with the side wall of the protrusion 26. As illustrated in FIGS. 2 and 3, in the present embodiment, substantially the entire side face of the protrusion 26 is covered with the side wall 34b of the upper cap member 34 and the lower cap member 36. Therefore, the side wall 34b of the upper cap member 34 and the entire lower cap member 36 form the side wall of the entire cap member 20.

In a mount state in which the cap member 20 is mounted on the protrusion 26, the lower cap member 36 is located between the side wall of the protrusion 26 and the guide member 18. More specifically, the lower cap member 36 is disposed opposite and adjacent to an inner side face 18a of the guide member 18 in a manner that the lower cap member 36 is vertically slidable along the inner side face 18a.

The lower cap member 36 further includes a flange 36b protruding outward in a portion above the upper edge of the guide member 18. The flange 36b covers a portion above a gap 40 between the lower cap member 36 and the inner side face 18a of the guide member 18. The flange 36b has a top face that is in contact with the lower face of the casing 16, particularly with the edge of the button hole 32. This configuration prevents the lower cap member 36 from passing through the button hole 32 and moving upward past the lower end of the casing 16.

In particular, the flange 36b may extend outward to a portion above the outer edge of the guide member 18 or further outward, as illustrated in FIG. 3.

The press button structure 10 according to the present embodiment has been described. The operation of the press button structure 10 and the effect of each component will be now described below.

Similar to the press button structure 110 according to the prior art example, pressing the top plate 34a of the upper cap member 34 by the user causes elastic deformation of the elastic member 28, thereby pressing the protrusion 26 downward. Contact of the movable contacts 30 disposed on the lower face of the protrusion 26 with the fixed contact 22 disposed on the substrate 12 triggers detection of operation of the press button.

The feeling curve for the press button structure 10 is similar to that shown in FIG. 7. Specifically, in the natural state in which the elastic member 28 has a skirt shape, between strokes 0 and S1, the load increases in accordance with the pressing amount of the protrusion 26. At stroke S1, the elastic member 28 changes its shape from the skirt shape to a horizontally extending shape or a horizontally parallel circular shape. Thereafter, the reaction force of the elastic member 28 decreases; therefore between strokes S1 and S2, the load decreases in accordance with the pressing amount of the protrusion 26. The upward reaction force of the elastic member 28 thus changes in accordance with the pressing amount of the protrusion 26 that is pressed downward. Specifically, the magnitude of the reaction force between strokes 0 and S1 and the magnitude of the reaction force between strokes S1 and S2 differ from each other, which provides a click feeling to the user. At stroke S2, the movable contacts 30 come into contact with the fixed contact 22, and thereafter (between strokes S2 and S3), the protrusion 26 moves due to elastic deformation of the elastic member 28 and the load increases. At stop of the user's depression of the protrusion 26, the stroke of the protrusion 26 returns to 0 due to an upward urging force of the elastic member 28.

In the press button structure 10, the guide member 18 is disposed immediately beside the outer side face of the lower cap member 36. Therefore, the user's pressing of the top plate 34a at an edge portion in a plan view brings the lower cap member 36 into contact with the guide member 18 to thereby reduce inclination of the protrusion 26. In other words, the protrusion 26 is prevented from being inclined while being allowed to move upward and downward. This configuration achieves a substantially proper feeling curve (see FIG. 7 or FIG. 8) with the user's pressing of the top plate 34a at any location, and thus reduces variations in the sense of pressing obtained by pressing different locations on the surface of the press button.

In particular, in the present embodiment, the guide member 18 that is made of POM has a small coefficient of friction. Therefore, the protrusion 26 can move upward and downward smoothly even with the lower cap member 36 in contact with the guide member 18.

To inhibit inclination of the protrusion 26, the gap 40 between the lower cap member 36 and the inner side face 18a of the guide member 18 is set to be significantly narrow, which is at least smaller than the gap 130 (see FIG. 6) between the side wall 118b of the cap member 118 and the inner side wall of the button hole 128 of the press button structure 110. This may cause foreign matter such as dust and echo jelly entering the gap 40 to fix therein and prevent the upward and downward movement of the lower cap member 36 or the protrusion 26.

In consideration of this disadvantage, in the present embodiment, the flange 36b covering the region above the gap 40 is disposed. This flange 36b inhibits entry of foreign matter into a gap 42 between the side wall 34b of the upper cap member 34 and the inner side wall of the button hole 32 from further entering the gap 40. The flange 36b that extends further to a region above the outer side edge of the guide member 18 further inhibits entry of the foreign matter into the gap 40. This reduces obstruction of the upward and downward movement of the protrusion 26 caused by the foreign matter. The gap 42 may have a width similar to that of the gap 130 of the press button structure 110.

It is also possible to employ a transparent top plate 34a of the upper cap member 34 and insert a sheet (now shown) with printed letters that indicate a function of the press button, for example, between the top plate 34a and the protrusion 26. Assuming that this sheet is to be changed with the change of the function of the press button, the cap member that is a single member which cannot be separated into the upper cap member 34 and the lower cap member 36 and that has the flange 36b is disadvantageous in that, to change the sheet, not only the cap member 20 but also the casing 16 needs to be removed.

In the present embodiment, the cap member 20 is composed of the upper cap member 34 and the lower cap member 36 having the flange 36b, and the upper cap member 34 and the lower cap member 36 are detachable. This configuration eliminates the need to remove the casing 16 to change the sheet; it is only necessary to remove the upper cap member 34 from the lower cap member 36. Therefore, in the present embodiment, sheet change can be easily performed.

The press button structure of an ultrasonic diagnostic apparatus according to the disclosure is not limited to the embodiment described above, and various modifications may be made without departing from the scope of the claims.

The invention claimed is:

1. A press button structure of an ultrasonic diagnostic apparatus, the press button structure comprising:
   a substrate including a fixed contact;
   a movable contact member disposed over the substrate, the movable contact member comprising:
      a base;
      a protrusion having a convex shape protruding upward, the protrusion having a movable contact on a lower face of the protrusion, the movable contact to be in contact with the fixed contact; and an elastic member connecting the base and the protrusion, the elastic member, in a natural state, urging the protrusion upward to hold the protrusion in a manner that the movable contact and the fixed contact are separated, the elastic member having an upward reaction force that changes in accordance with a pressing amount of the protrusion that is pressed downward, a cylindrical guide member disposed to surround a side of the protrusion; and a cap member mounted on the protrusion, the cap member comprising a top plate covering a top face of the protrusion and a side wall covering a side face of the protrusion, wherein the side wall of the cap member includes a flange that protrudes outwardly in a region above an upper edge of the guide member and covers an upper part of a gap between the side wall of the cap member and an inner side face of the guide member, and the side wall of the cap member extends further downward relative to the flange and is disposed adjacent and opposite an inner side face of the guide member in a manner that the side wall is slidable upward and downward along the inner side face of the guide member.

2. The press button structure of an ultrasonic diagnostic apparatus according to claim 1, wherein
the flange extends to a point above an outer edge of the guide member.

3. The press button structure of an ultrasonic diagnostic apparatus according to claim 1, further comprising:
a casing disposed over the movable contact member and having a button hole to allow the cap member to pass through, wherein the cap member comprises:
an upper cap member including the top plate, the upper cap member being inserted through the button hole; and
a lower cap member disposed below the casing and including the flange, and
wherein the upper cap member and the lower cap member are detachable.

4. The press button structure of an ultrasonic diagnostic apparatus according to claim 1, wherein
the protrusion has an elongated shape extending along one direction in a plan view.

* * * * *